US008523040B2

(12) United States Patent  
Crainich et al.

(10) Patent No.: US 8,523,040 B2  
(45) Date of Patent: Sep. 3, 2013

(54) FASTENER AND FASTENER APPLIER HAVING SELECTIVE SUTURE ATTACHMENT

(75) Inventors: Lawrence Crainich, Charlestown, NH (US); Mark S. Zeiner, Mason, OH (US); Michael J. Stokes, Cincinnati, OH (US); Jason L. Harris, Mason, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 672 days.

(21) Appl. No.: 12/113,644

(22) Filed: May 1, 2008

(65) Prior Publication Data

US 2009/0272783 A1   Nov. 5, 2009

(51) Int. Cl.  
*A61B 17/068*   (2006.01)

(52) U.S. Cl.  
USPC .................................. 227/175.1; 227/176.1

(58) Field of Classification Search  
USPC .......... 227/175.1, 176.1, 177.1, 179.1, 180.1; 606/143, 139  
See application file for complete search history.

(56) References Cited

U.S. PATENT DOCUMENTS

| | | | | |
|---|---|---|---|---|
| 2,741,766 A | * | 4/1956 | Mott | 227/77 |
| 2,775,763 A | * | 1/1957 | Flammer | 227/77 |
| 3,144,655 A | * | 8/1964 | Kent | 227/77 |
| 4,841,960 A | * | 6/1989 | Garner | 606/75 |
| 5,571,117 A | * | 11/1996 | Ahn | 606/139 |
| 5,573,543 A | * | 11/1996 | Akopov et al. | 606/144 |
| 5,634,584 A | | 6/1997 | Okorocha et al. | |
| 5,662,662 A | * | 9/1997 | Bishop et al. | 606/143 |
| 5,829,662 A | | 11/1998 | Allen et al. | |
| 6,702,826 B2 | * | 3/2004 | Liddicoat et al. | 606/151 |
| 2002/0042621 A1 | | 4/2002 | Liddicoat et al. | |
| 2007/0032822 A1 | * | 2/2007 | Ortiz et al. | 606/219 |
| 2007/0043384 A1 | * | 2/2007 | Ortiz et al. | 606/142 |

FOREIGN PATENT DOCUMENTS

| | | |
|---|---|---|
| EP | 0536903 | 4/1993 |
| EP | 1754444 | 2/2007 |
| WO | WO 96/27332 | 9/1996 |

OTHER PUBLICATIONS

PCT International Search Report and Written Opinion, Jun. 29, 2009 (16 pgs.).

* cited by examiner

*Primary Examiner* — Alexandra Elve  
*Assistant Examiner* — Nathaniel Chukwurah  
(74) *Attorney, Agent, or Firm* — Welsh Flaxman & Gitler LLC

(57) ABSTRACT

A surgical stapling device for deploying staples connected with suture to tissue includes a handle having a staple actuator mechanism, a tubular support shaft having a longitudinal axis and extending from the handle, and a staple cartridge mounted on the support shaft and connected to the staple actuator mechanism for applying one or more staples to the tissue. The cartridge has a cartridge housing adapted to receive a plurality of staples in a row for longitudinal movement therethrough and an anvil mounted on the housing. The cartridge further includes a mechanism for advancing the forwardmost staple in the row into engagement with the anvil, and a suture guide supporting a length of suture that extends in a loop for attachment to the staples as they are secured to the tissue.

9 Claims, 14 Drawing Sheets

FASTENER AND FASTENER APPLIER HAVING SELECTIVE SUTURE ATTACHMENT

BACKGROUND OF THE INVENTION

1. Field of the Invention

The present invention relates to a fastener and fastener applier. More particularly, the invention relates to a fastener and fastener applier wherein staples and sutures are simultaneously applied in the performance of gastric reduction surgery, general tissue manipulation and apposition or related procedures.

2. Description of the Related Art

Obesity is a medical condition affecting more than 30% of the population in the United States. Obesity affects an individual's personal quality of life and contributes significantly to morbidity and mortality. Obese patients, i.e., individuals having a body mass index ("BMI") greater than 30, often have a high risk of associated health problems (e.g., diabetes, hypertension and respiratory insufficiency), including early death. With this in mind, and as those skilled in the art will certainly appreciate, the monetary and physical costs associated with obesity are substantial. In fact, it is estimated the costs relating to obesity are in excess of 100 billion dollars in the United States alone. Studies have shown that conservative treatment with diet and exercise alone may be ineffective for reducing excess body weight in many patients. Bariatrics is the branch of medicine that deals with the control and treatment of obesity. A variety of surgical procedures have been developed within the bariatrics field to treat obesity. The most common currently performed procedure is the Roux-en-Y gastric bypass (RYGB). This procedure is highly complex and is commonly utilized to treat people exhibiting morbid obesity. In an RYGB procedure a small stomach pouch is separated from the remainder of the gastric cavity and attached to a resectioned portion of the small intestine. This resectioned portion of the small intestine is connected between the "smaller" gastric cavity and a distal section of small intestine allowing the passage of food therebetween. The conventional RYGB procedure requires a great deal of operative time. Because of the degree of invasiveness, postoperative recovery can be quite lengthy and painful. Still more than 100,000 RYGB procedures are performed annually in the United States alone, costing significant health care dollars.

In view of the highly invasive nature of the RYGB procedure, other less invasive procedures have been developed. These procedures include gastric banding, which constricts the stomach to form an hourglass shape. This procedure restricts the amount of food that passes from one section of the stomach to the next, thereby inducing a feeling of satiety. A band is placed around the stomach near the junction of the stomach and esophagus. The small upper stomach pouch is filled quickly, and slowly empties through the narrow outlet to produce the feeling of satiety. Other forms of bariatric surgery that have been developed to treat obesity include Fobi pouch, bilio-pancreatic diversion and gastroplasty or "stomach stapling".

Morbid obesity is defined as being greater than 100 pounds over one's ideal body weight. For individuals in this category, RYGB, gastric banding or another of the more complex procedures may be the recommended course of treatment due to the significant health problems and mortality risks facing the individual. However, there is a growing segment of the population in the United States and elsewhere who are overweight without being considered morbidly obese. These persons may be 20-30 pounds overweight and want to lose the weight, but have not been able to succeed through diet and exercise alone. For these individuals, the risks associated with the RYGB or other complex procedures often outweigh the potential health benefits and costs. Accordingly, treatment options should involve a less invasive, lower cost solution for weight loss.

It is also known to create cavity wall plications through endoscopic only procedures. However, operating solely within the interior of the gastric cavity limits the plication depth that can be achieved without cutting. Furthermore, access and visibility within the gastric and peritoneal cavities is limited in a purely endoscopic procedure as the extent of the reduction increases.

With the foregoing in mind, it is desirable to provide surgical weight loss procedures (and related medical instrument) that are inexpensive, with few potential complications, and that provide patients with a weight loss benefit while buying time for the lifestyle changes necessary to maintain the weight loss. Further, it is desirable that the procedures be minimally invasive to the patient, allowing for a quick recovery and less scarring. The present invention provides procedures and a medical instrument for the efficient and effective performance of surgical weight loss procedures.

SUMMARY OF THE INVENTION

It is, therefore, an object of the present invention to provide a surgical stapling device including an actuator handle assembly coupled to a staple head assembly. The staple head assembly includes a cartridge housing adapted to receive a plurality of staples in a row for longitudinal movement therethrough; an anvil mounted on the housing; a mechanism for advancing the forwardmost staple in the row into engagement with the anvil; and a suture guide supporting a length of suture that extends in a loop for selective attachment to the staples as the staples are deployed.

It is also an object of the present invention to provide a surgical stapling device including a staple former for forming the forwardmost staple about the anvil.

It is another object of the present invention to provide a surgical stapling device wherein each staple includes a crimp loop.

It is a further object of the present invention to provide a surgical stapling device including a crimping arm which selectively engages the crimp loop to securely lock the staple relative to the length of suture.

It is also an object of the present invention to provide a surgical stapling device wherein the crimping arm includes an outer crimping arm member and an inner crimping arm member.

It is another object of the present invention to provide a surgical stapling device wherein the outer crimping arm member moves relative to the inner crimping arm member to compress a distal end of the inner crimping arm member about the crimp loop for closing the crimp loop about the suture.

It is a further object of the present invention to provide a surgical stapling device including a crimping arm which selectively engages the suture to securely lock the staple relative to the suture.

It is also an object of the present invention to provide a surgical stapling device wherein each of the staples includes a backspan with first and second legs, and the backspan of the staple is provided with a crimp loop shaped and dimensioned for receiving and securing the suture.

It is another object of the present invention to provide a surgical stapling device wherein the suture guide supports the suture that extends in a loop from a proximal end of the surgical stapling device such that it may be secured to the staples as the staples are deployed.

It is a further object of the present invention to provide a surgical stapling device wherein the suture guide includes an upper suture strand guide track and a lower suture strand guide track separated to expose a portion of the suture which may be secured to the staple.

It is also an object of the present invention to provide a method for tissue apposition including applying a series of staples to tissue, simultaneously applying a suture with application of the series of staples, and selectively crimping at least one staple to lock the suture relative to the staple.

It is another object of the present invention to provide a method wherein the staple includes a crimp loop which is crimped in a manner locking the suture relative to the staple.

It is a further object of the present invention to provide a method wherein the step of applying includes applying a first staple and crimping the staple to the suture at one end of a desired tissue apposition location along a tissue span.

It is also an object of the present invention to provide a method wherein the tissue span in on a stomach.

It is another object of the present invention to provide a method wherein the method is applied as part of a gastric volume reduction procedure.

It is a further object of the present invention to provide a method wherein the step of applying includes applying uncrimped staples on alternating sides of the desired tissue apposition location along an entire length of the desired fold location.

It is also an object of the present invention to provide a surgical stapling method including the step of tensioning by pulling upon the suture to draw the staples together and fold the tissue.

It is another object of the present invention to provide a surgical stapling method including the step of crimping a final staple to secure the suture to the staple while maintaining the suture under tension.

Other objects and advantages of the present invention will become apparent from the following detailed description when viewed in conjunction with the accompanying drawings, which set forth certain embodiments of the invention.

BRIEF DESCRIPTION OF THE DRAWINGS

FIGS. 21, 22, 23 and 24 respectively show the staple in its starting orientation, folded orientation and crimped orientation.

DESCRIPTION OF THE PREFERRED EMBODIMENT

The detailed embodiment of the present invention is disclosed herein. It should be understood, however, that the disclosed embodiment is merely exemplary of the invention, which may be embodied in various forms. Therefore, the details disclosed herein are not to be interpreted as limiting, but merely as a basis for teaching one skilled in the art how to make and/or use the invention.

In accordance with the present invention, and with reference to FIGS. 1 to 21, a surgical stapling device 10 is disclosed for deploying staples 12 in conjunction with a suture 14 connected thereto. As will be better appreciated based upon the following disclosure, the surgical stapling device 10 provides for the ability to selectively secure the staple 12 with the suture 14 in either a relatively sidable configuration or a crimped (locked) configuration. As a result, the staple 12, when formed in accordance with a preferred embodiment of the present invention, can be selectively formed to crimp around the suture 14 at desired locations, while subsequently adding staples at additional locations along the same length of suture 14 allowing for the stapling of tissue while simultaneously linking the various staple sites with the length of suture 14. For example, and as discussed below in greater detail, a tissue fold is created by applying a series of staples 12 to tissue on opposite sides of the span of tissue to be folded and simultaneously applying a suture 14 with the application of the series of staples 12. While applying the staples 12 and suture 14 at least one staple 12 is crimped to securely lock the suture 14 relative to the staple 12. Thereafter, the suture 14 may be pulled to draw the series of staples 12 together causing the tissue to fold in a desired manner.

Figure 22:
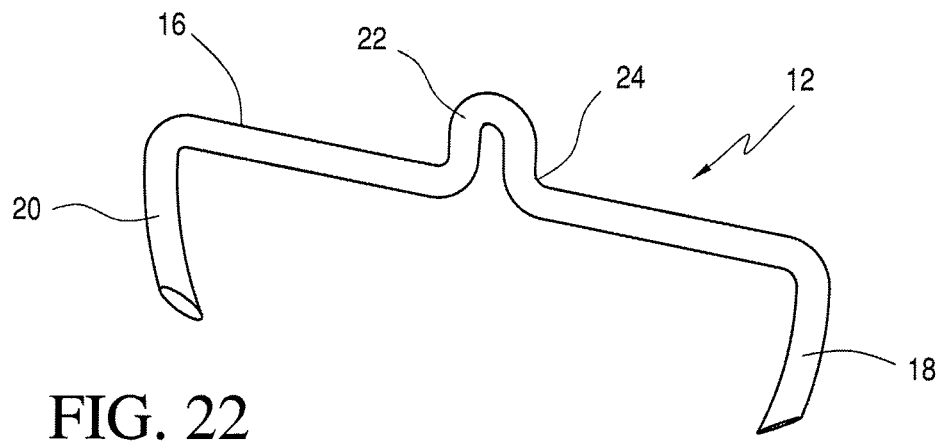
Figure 23:
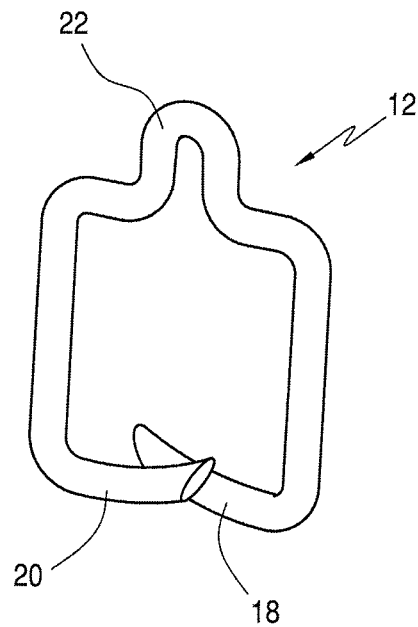
Figure 24:
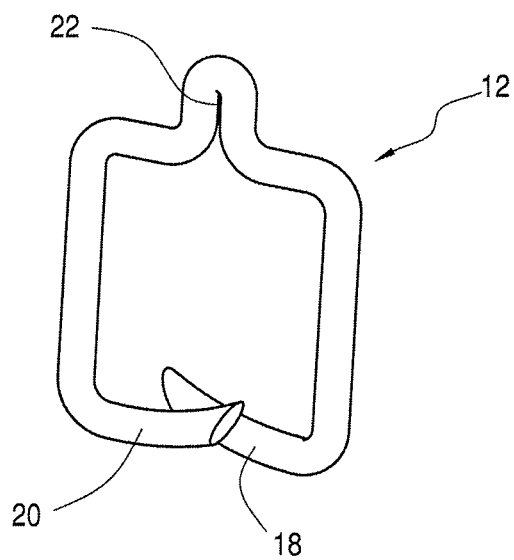

In accordance with a preferred embodiment of the present invention, and with reference to FIGS. 22 to 24, a modified box staple 12 is employed. The staple 12 includes a backspan 16 with first and second legs 18, 20 extending therefrom. The first and second legs 18, 20 extend substantially perpendicularly from the longitudinal axis of the backspan 16. The first and second legs 18, 20 also lie in substantially the same plane.

The backspan 16 of the staple 12 is provided with a crimp loop 22 shaped and dimensioned for receiving and securing a suture 14 in a manner discussed below in greater detail. The crimp loop 22 is positioned along a central portion 24 of the backspan 16 and is preferably oriented to lie within the same plane as the first and second legs 18, 20.

The surgical stapling device 10 includes a staple head assembly 26 connected to an actuator handle assembly 210 via a support shaft 216. Although preferably rigid in construction, it is envisioned that support shaft 216 may be flexible in nature allowing delivery and controlled positioning of staple head assembly 26 for natural orifice (transoral, transvaginal, etc.) surgical procedures. The staple head assembly 26 includes a first end 28 and a second end 30, wherein staples 12 are moved within a staple cartridge housing 32 of the staple head assembly 26 from the second end 30 thereof toward the first end 28 thereof for subsequent dispensing and fastening as discussed below in greater detail.

The staple head assembly 26 includes a staple cartridge housing 32 in which a plurality of staples 12 (or other fasteners) are housed. The staples 12 are supported upon a track 34. The track 34 includes a first staple recess 36 and a second staple recess 38. The respective first staple recess 36 and second staple recess 38 are shaped and dimensioned for providing clearance for the legs 18, 20 of the staples 12, and the first and second staple recesses 36, 38 are therefore substantially parallel.

The staples 12 are maintained in position within the track 34 of the staple head assembly 26 under the control of first and second staple springs 40, 42. The first and second staple springs 40, 42 act upon buttons (not shown) that act upon the staples 12 held within the track 34 to continually apply a biasing force moving the staples 12 toward the dispensing, first end 28 of the staple head assembly 26. With this in mind, the track 34 is provided with first and second spring recesses 44, 46 in which the respective first and second staple springs 40, 42 are housed. Each of the first and second staple springs 40, 42 include a first end 48, 52 and a second end 50, 54 wherein the first end 48, 52 is supported by a wall 56, 58 at the respective closed ends of the first and second spring recesses 44, 46 and the second end 50, 54 of the respective staple springs 40, 42 contact the buttons (not shown) that contact the staples 12 applying force to the staples 12 in a direction toward the first end 28 of the staple head assembly 26.

Formation of the staples 12 for dispensing and attachment to tissue in accordance with the present invention is achieved at the first end 28 of the staple head assembly 26 under the control of an actuation assembly 60 forcing the forwardmost staple 12 into a forming recess where the respective legs 18, 20 of the staple 12 are folded to secure the staple 12 to a desired portion of tissue.

Adjacent the first end 28 of the staple head assembly 26 is a suture guide 62. The suture guide 62 supports a length of suture 14 that extends in a loop from the proximal end of the surgical stapling device 10 such that it may be secured to the staples 12 as they are deployed and secured to the tissue. In particular, the suture guide 62 is composed of a track in which the suture 14 is looped for crimping with the staple head assembly 26. In particular, the staple guide 62 includes an upper suture strand guide track 64 and a lower suture strand guide track 67. The upper suture strand guide track 64 is separated from the lower suture strand guide track 67 adjacent the first end 28 of the staple head assembly 26 exposing a portion of the suture 14 which is secured to a staple 12 in a manner discussed below in greater distal.

More particularly, and with reference to the sequence of steps shown in FIGS. 2 to 13, the surgical stapling device 10 secures staples 12 to tissue while simultaneously laying down the suture 14 held by the suture guide 62 to the staple 12 and selectively allowing a medical practitioner to crimp the staple 12 onto the strand of suture 14 for locking that staple in position relative to the length of suture 14. The surgical stapling device 10 functions in a manner similar to commonly owned U.S. Pat. No. 5,829,662, entitled "ENDOSCOPIC SURGICAL STAPLING INSTRUMENT WITH PIVOTABLE AND ROTATABLE STAPLE CARTRIDGE", which is incorporated herein by reference.

The staple head assembly 26 includes a staple cartridge 68. The staple cartridge 68 includes a hollow cylindrical staple cartridge housing 32 that is tapered at its distal end. Preferably, the staple cartridge housing 32 is a one-piece molded plastic member. A hollow, generally cylindrical cartridge retainer 72 is inserted into the open proximal end of the staple cartridge housing 32 for closing off the staple cartridge housing 32 and coupling the staple head assembly 26 to the proximal section of the surgical stapling device. The cartridge retainer 72 includes a pair of spring-like latch arms 74 located at diametrically opposed positions at the front of the cartridge retainer 72. The latch arms 74 are snap-fitted into a pair of diametrically opposed openings 76 adjacent to the proximal end of the staple cartridge housing 32 to hold the staple cartridge housing 32 and the cartridge retainer 72 together. The cartridge retainer 72 includes an annular flange 78 which is received in the annular grooves 80 of the clamshell members 82, 84 to allow the staple cartridge 68 to rotate about its longitudinal axis relative to the support tube 86 and to the pivot connection 88. A set of twelve uniformly spaced circumferential teeth 90 is formed at the proximal end of the cartridge retainer 72. The teeth 90 are engaged by the detent arms 92 on the clamshell members 82, 84. The detent arms 92 and teeth 90 provide a ratchet mechanism that allows the rotational orientation of the staple cartridge 68 to be adjusted in increments of 30 degrees.

Inside the staple cartridge 68 is mounted a staple forming mechanism comprising an anvil 94, a staple holder 96 and a staple former 98 which are preferably made of stainless steel. The staple former 98 is channel-shaped and configured for sidably receiving the staple holder 96 therein. The staple former 98 has an elongated central slot 100 with an upstanding prong 102 at the proximal end of the slot 100. The staple holder 96 includes a depending prong 104 which is slidably received in the slot 100 and is biased away from the prong 102 by a compression coil spring 106. The first and second staple springs 40, 42 respectively mounted within the first and second springs recesses 44, 46 urge a series of staples 12 toward the distal end of the staple cartridge 68. As discussed above, the first and second staple springs are biased in the distal direction for maintaining the staples 12 in a desired configuration.

The staple driver arm 108 is connected to the staple former 98 by a plunger 110 which is sidably mounted between the clamshell members 82, 84. The plunger 110 is a generally flat metal plate, e.g., aluminum, and includes a longitudinally extending side flange 112 slidably received in a longitudinal groove 114 formed in the clamshell member 84. The plunger 110 has a pivot hole 116 adjacent to its proximal end. A pivot link 118 includes a pair of laterally projecting pivot pins 120, 122 which are pivotally received in the pivot holes 124, 116, respectively, to attach the staple driver 108 to the plunger 110. The pivot link 118 transfers the longitudinal movement of the staple driver 108 into longitudinal movement of the plunger 110. Also, the pivot link 118 permits the plunger 110 to pivot relative to the staple driver 108. At the distal end of the plunger 110, a smaller diameter front disk 128 is spaced from a larger diameter rear disk 130. The front disk 128 is inserted between a pair of inwardly projecting fingers 132 at the proximal end of the staple former 98 to transfer the longitudinal movement of the plunger 110 into longitudinal movement of the staple former 98. The front disk 128 and the inwardly projecting fingers 132 permit the staple former 98 to rotate relative to the plunger 110.

The staple cartridge housing 32 has an elongated hollow cylindrical wall 134 which preferably consists of transparent plastic material. Extending longitudinally inside the staple cartridge housing 32 is a first pair of elongated upstanding flanges 136 which are spaced apart and extend parallel to the longitudinal axis of the cylindrical wall 134. The elongated flanges 136 provide a set of guide rails, and define the first and second spring recesses 44, 46, for slidably supporting the staples 12 for longitudinal movement relative to the staple cartridge housing 32. Each flange or guide rail 136 has a ledge 138 which is inclined at an angle to the axis of the staple cartridge housing 32 and terminates in an extension 140 of the guide rail 136 at the open distal end of the staple cartridge housing 32. Each of the flanges 136 is spaced inwardly from the cylindrical wall 134 to provide a pair of elongated side channels 142 for receiving the depending legs 18, 20 of the staples 12. The staple cartridge housing 32 includes a second pair of depending upper flanges 144 which are spaced apart and extend parallel to the longitudinal axis of the outer cylindrical wall 134. The upper flanges 144 terminate above the lower flanges 136 to provide a sufficient clearance therebetween to receive the crimp loop 22 of the staples 12. On the inside of each lower flange 136 is an elongated ledge 138 that sidably supports the staple former 98.

The staple cartridge housing 32 has a tapered nose 146 at its distal end including an internal horizontal ledge 148 provided with a longitudinal channel 150 for receiving the anvil 94 of the staple head assembly 26. The ledge 148 has a rearwardly projecting post 152 to which the anvil 94 is secured. The tapered nose 146 has a central depending guide tab 154 located above the ledge 148 and provided with a downwardly sloped rear edge 156 which serves as a guide for the crimp loop 22 of the staple 12 advanced by the staple forming mechanism. Also, the tapered nose 146 includes a pair of sloped ramps 158 on opposite sides of the central guide tab 154 for engaging the backspan 16 of the staple 12 which is advanced by the staple forming mechanism to pivot the staple 12 into an orientation parallel to the longitudinal axis of the staple cartridge housing 32. Each of the ramps 158 terminate at a ledge 160 located adjacent to one of the extensions 140 of the guide rails 136. A window 162 is formed on each side of the staple cartridge housing 32 adjacent to one of the ramps 158 as a result of the molding process used to form the staple cartridge housing 32.

The staple former 98 is an elongated, channel-shaped member provided with upstanding side flanges 65 extending along its opposite sides. The staple holder 96 is an elongated plate-like member that is sidably supported on the staple former 98 and located between the side flanges 65. The compression coil spring 106 normally biases the staple holder 96 distally relative to the staple former 98 with the depending prong 104 biased against prong 102 at the distal end of the elongated central slot 100. The staple holder 96 and the staple former 98 are inserted into the staple cartridge 68 between the lower upstanding flanges 136. The staple former 98 is sidably supported on the ledges 138 formed on the inside of the flanges 136. An ejector arm 166 extending from the distal end of the staple holder 96 has a notch 168 for receiving the crimp loop 22 of the staple 12. A pusher finger 170 projects forwardly into the notch 168 at the distal end of the staple holder 96 for engaging the crimp loop 22 of the staple 12 as the staple holder 96 is advanced to move the staple 12 into engagement with the anvil 94. The distal end of the ejector arm 166 is slanted away from and above the level of the pusher finger 170 and serves to disengage the staple 12 from the anvil 94 as the staple holder 96 is retracted after the staple 12 is formed. A pair of fingers 172 at the tip of the ejector arm 166 is spaced apart to receive the depending tab 174 of the staple cartridge housing 32 therebetween.

The anvil 94 includes a pair of laterally spaced anvil prongs 176 at its distal end which allow the ejector arm 166 to pass therebetween when the staple holder 96 is advanced. Each anvil prong 176 includes a ramp 178 for guiding the crown of the staple 12 into engagement with the proximal side of the anvil prong 176. In addition, the spacing between the anvil prongs 176 and the spacing between the fingers 172 at the tip of the ejector arm 166 provide a location through which the suture 14 is passed for engagement with the crimp loop 22 in accordance with the present invention as discussed below in greater detail.

Figure 1:
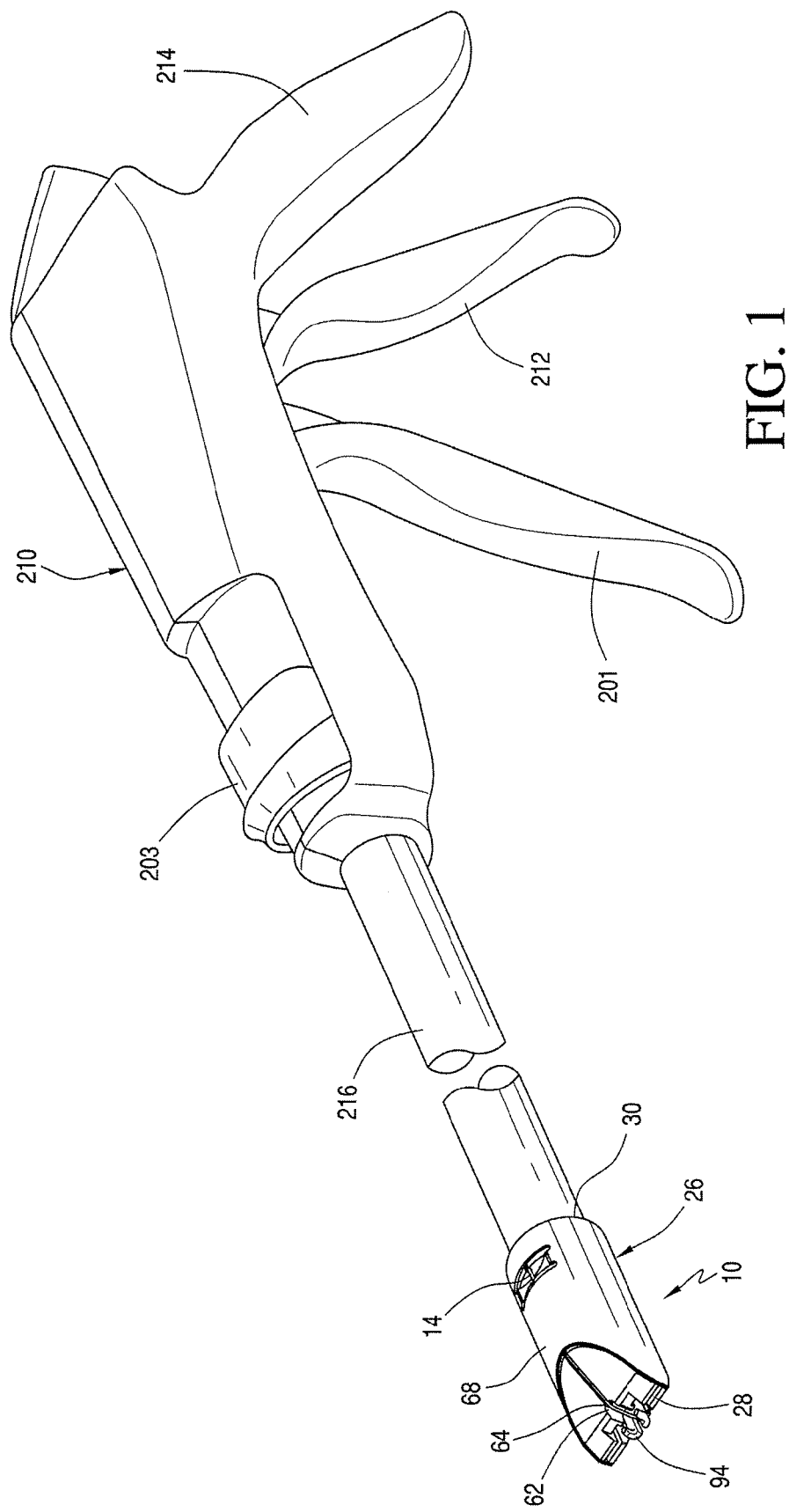
FIG. 1 is a perspective view of the surgical stapling device in accordance with the present invention.
Figure 2:
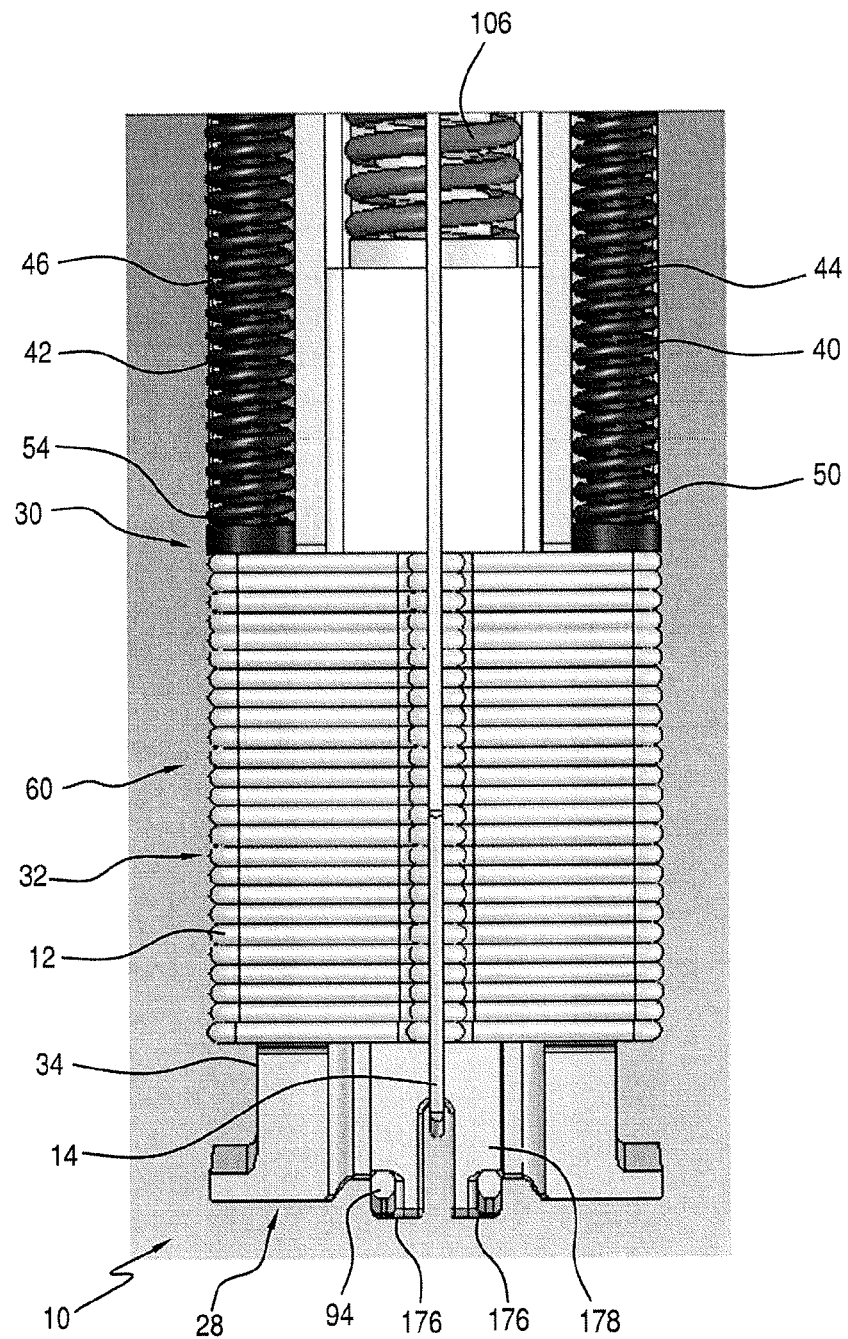
FIGS. 2, 3 and 4 are respectively a sectional top view, a cross sectional view and a sectional perspective view of the present surgical stapling device in its starting configuration prior to actuation of the staple forming mechanism.
Figure 3:
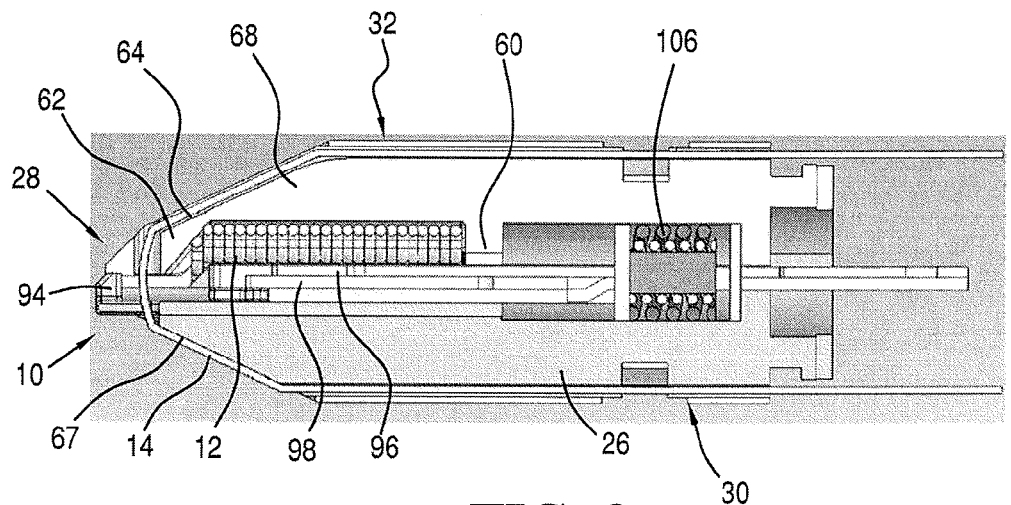
Figure 4:
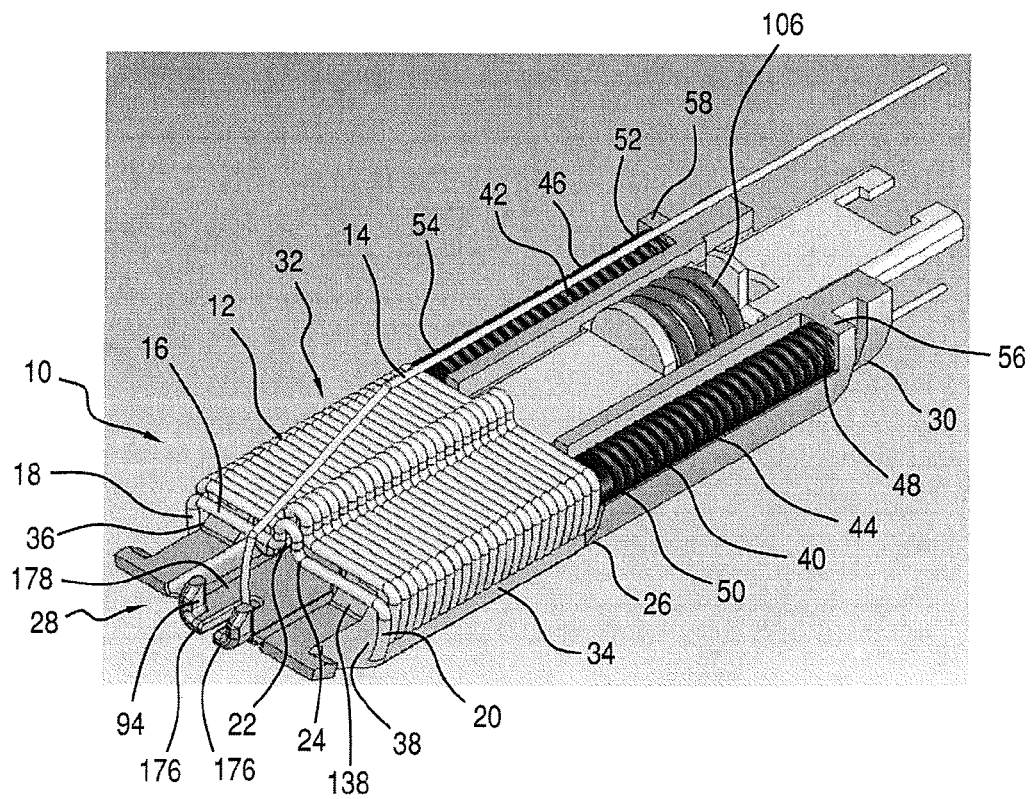

Referring to FIGS. 2, 3 and 4, a stack of staples 12 is mounted in the staple cartridge housing 32 with the backspans 16 of the staples 12 resting on and slidably supported by the elongated flanges or guide rails 136. The crimp loop 22 of the staples 12 sits above the staple holder 96. The row of staples 12 is urged forwardly toward the distal end of the staple cartridge housing 32 by the first and second staple springs 40, 42 functioning as a staple follower. The staple former 98 is biased rearwardly by a return spring in the actuator handle assembly 210 to urge the prong 102 against the front of the cartridge retainer 72. The staple holder 96 is biased forwardly by the compression coil spring 106 that urges the depending prong 104 against the front edge of the slot 100 in the staple former 98. The ejector arm 166 at the distal end of the staple holder 96 is located adjacent to the guide tab 154 at the front of the tapered nose 146 of the staple cartridge housing 32.

As shown in FIGS. 3 and 4, the offset or crimp loop 22 of the forwardmost staple 12 is located at a level different from the remaining staples 12 in the stack. The crimp loop 22 of the forwardmost staple 12 is engaged by the notch 168 in front of the pusher finger 170. When the staple holder 96 is advanced, the crimp loop 22 of the forwardmost staple 12 is advanced by the pusher finger 170. The backspan 16 of the forwardmost staple 12 is advanced along a path to rotate the staple 12 by 90 degrees about its crimp loop 22.

Figure 5:
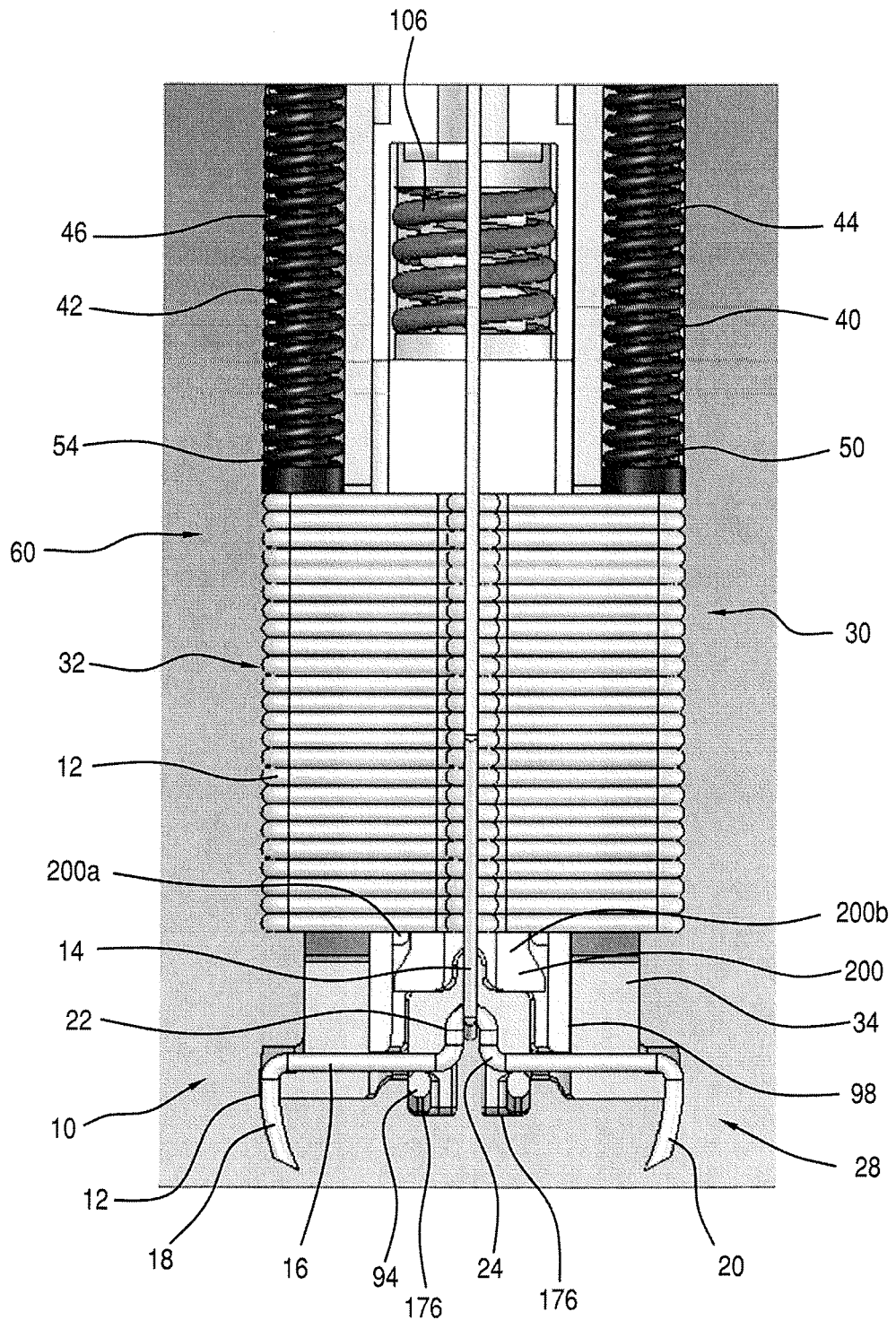
FIGS. 5, 6 and 7 are respectively a top sectional view, a cross sectional view and a perspective sectional view of the surgical stapling device with the staple in its forward pre-folded configuration.
Figure 6:
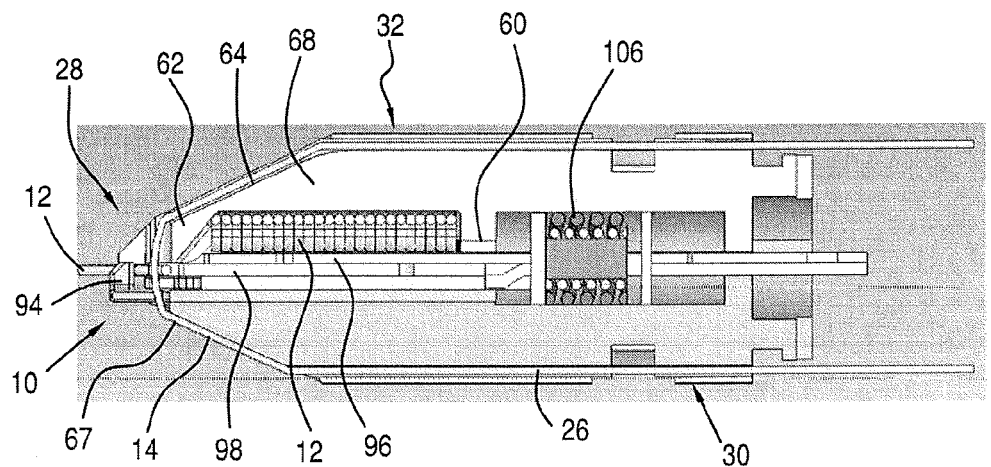
Figure 7:
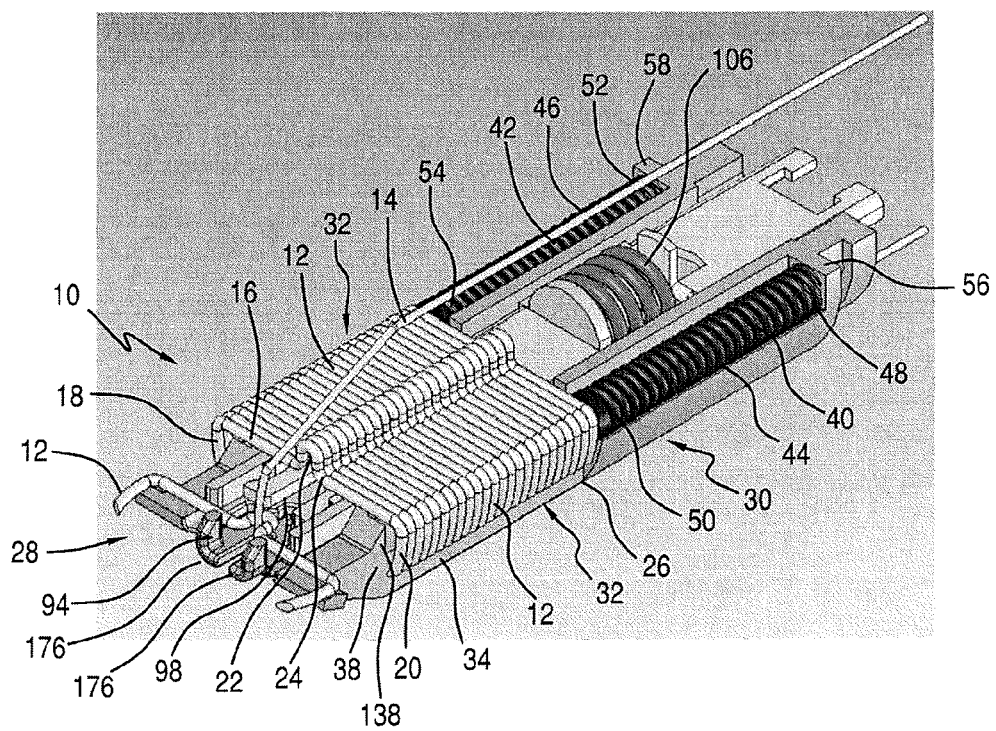
Figure 8:
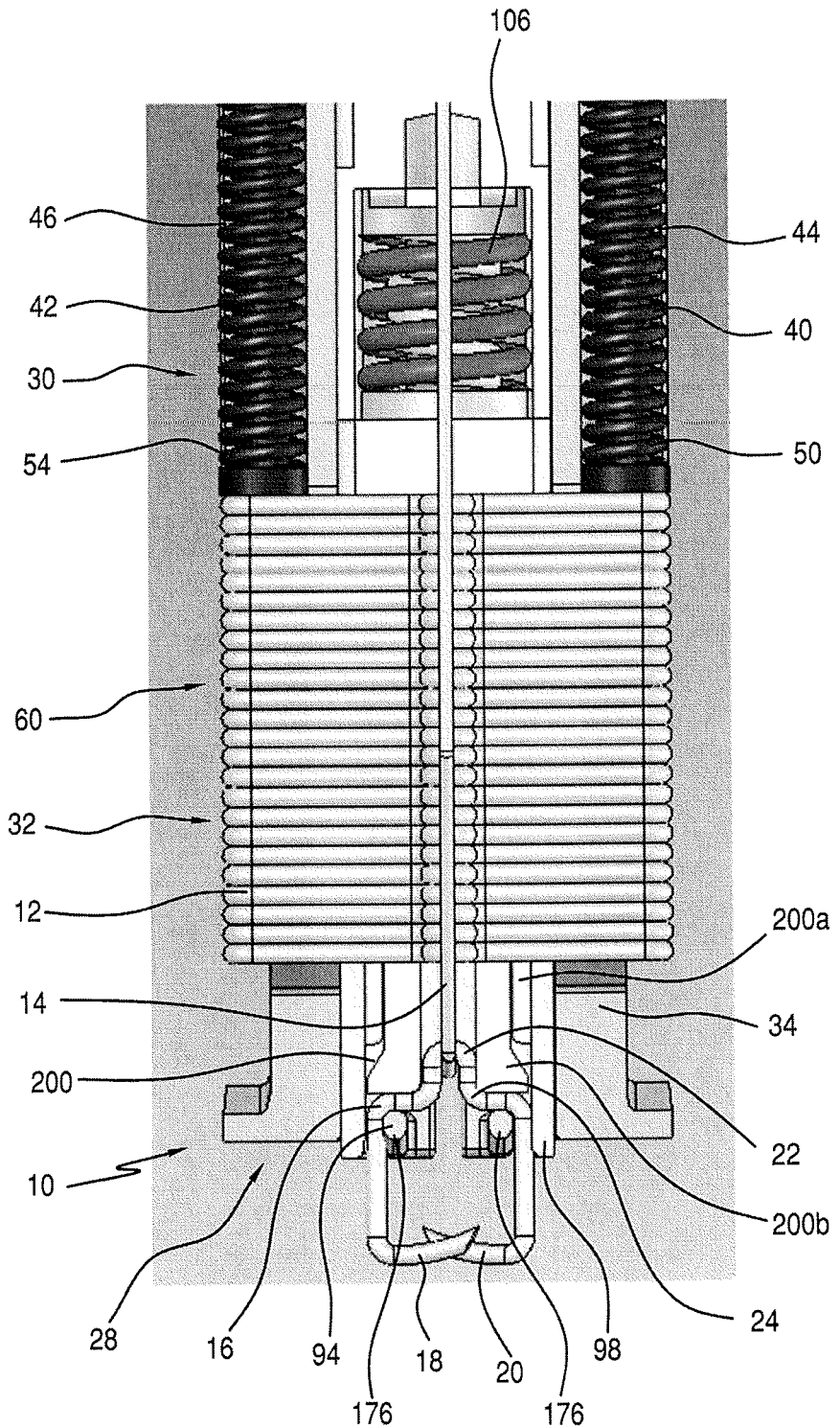
FIGS. 8, 9 and 10 are respectively a sectional top view, a cross sectional view and a sectional perspective view of the present surgical stapling device with the staple folded (but prior to crimping of the crimp loop).
Figure 9:
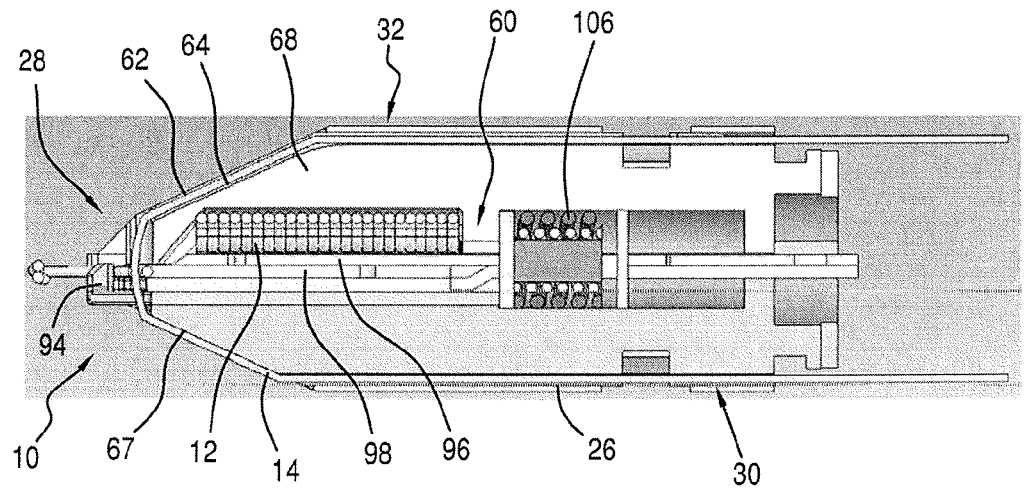
Figure 10:
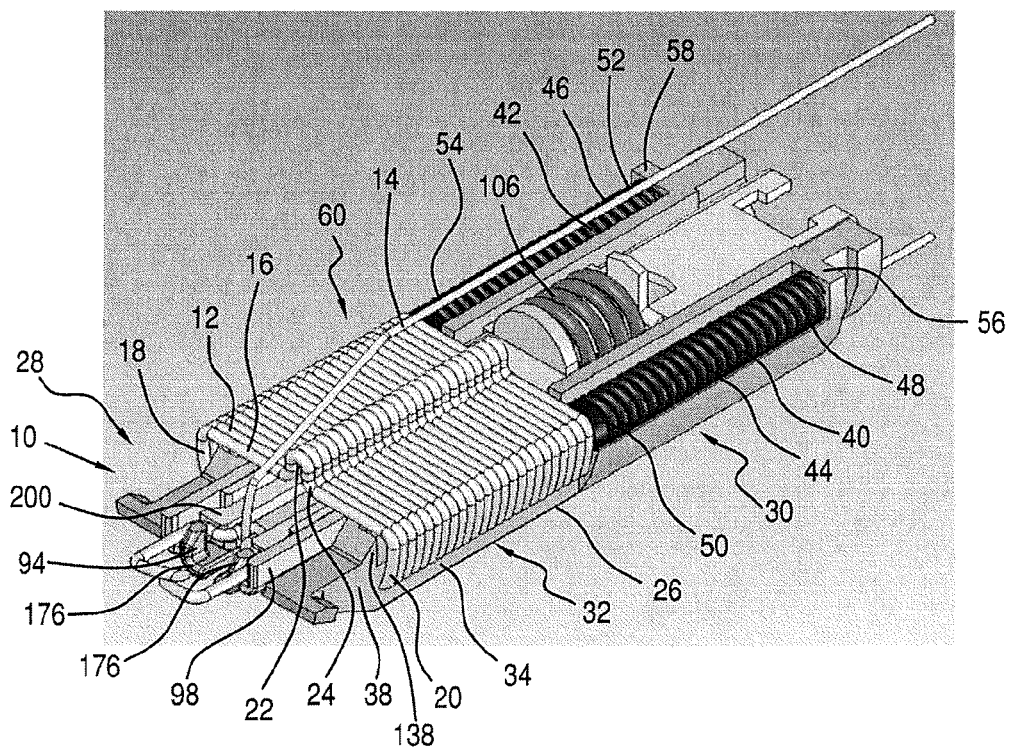

As shown in FIGS. 5, 6 and 7, with the staple holder 96 partially advanced, the forwardmost staple 12 is rotated into a longitudinal orientation with its staple legs 18, 20 parallel to the longitudinal axis of the staple cartridge housing 32. In addition, because of the positioning of the suture guide, the suture 14 is positioned within the crimp loop 22. Thereafter, as shown in FIGS. 8, 9 and 10, when the staple holder 96 is fully advanced, the forwardmost staple 12 travels along the extensions 140 of the guide rails 136 and is clamped against the anvil prongs 176 with the staple legs 18, 20 projecting distally from the front of the staple cartridge housing 32. The remaining staples 12 in the stack are restrained by the top of the staple holder 96 that engages the staples 12.

The staple forming mechanism of the staple cartridge 68 is actuated by squeezing the staple actuating lever 212 toward the handle grip 214. As a result, the staple actuating lever 212 is pivoted about a pivot pin to advance the staple driver 108 in the distal direction that, in turn, advances the plunger 110 to actuate the staple holder 96 and the staple former 98.

The operation of the staple forming mechanism is illustrated in even greater detail in commonly owned U.S. Pat. No. 5,829,662.

After the staple 12 is completely formed, a decision must be made with regard to suture tension and termination of the suture line. If the goal is to allow the suture 14 to freely move relative to the staples 12 applied in accordance with the present invention, the staple actuating lever 212 is released for completion of the staple applying process.

Figure 11:
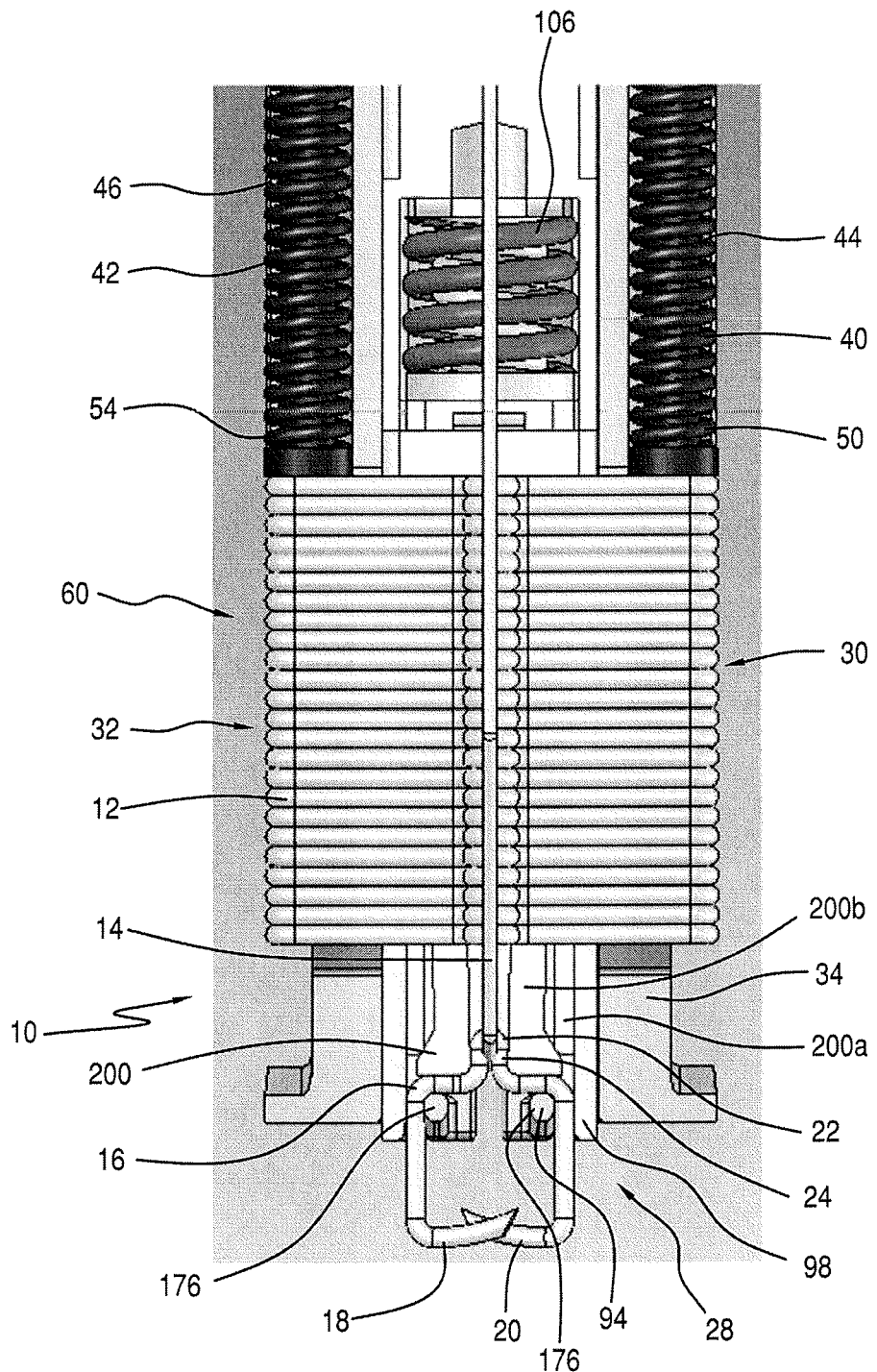
FIGS. 11, 12 and 13 are respectively a sectional top view, a cross sectional view and a sectional perspective view of the present surgical stapling device with the crimp loop crimped.
Figure 12:
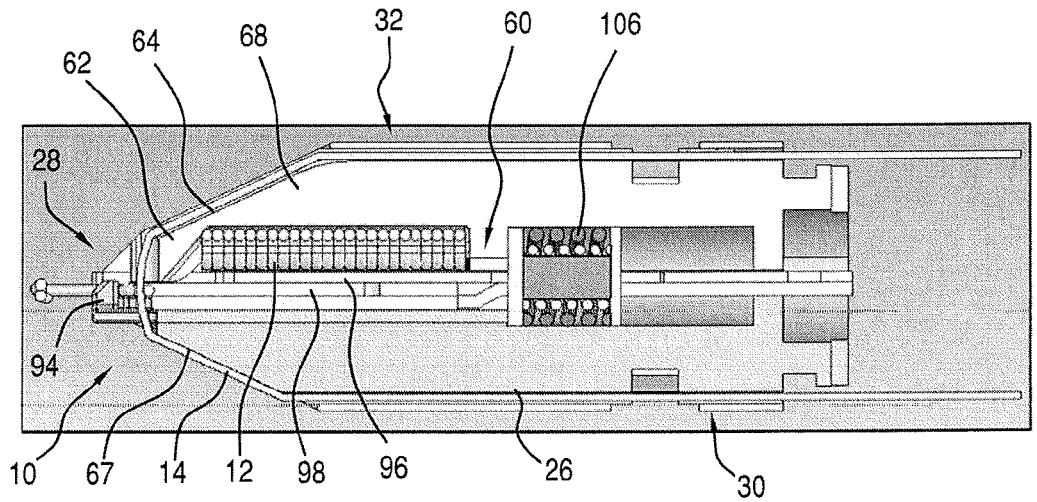
Figure 13:
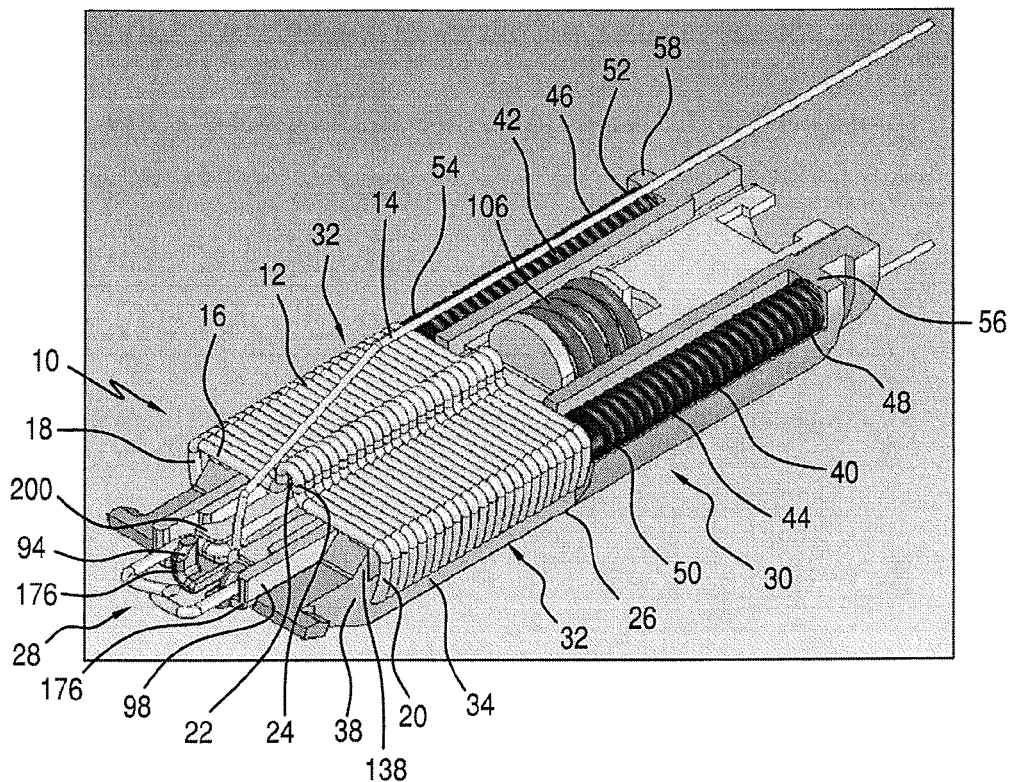
Figure 14:
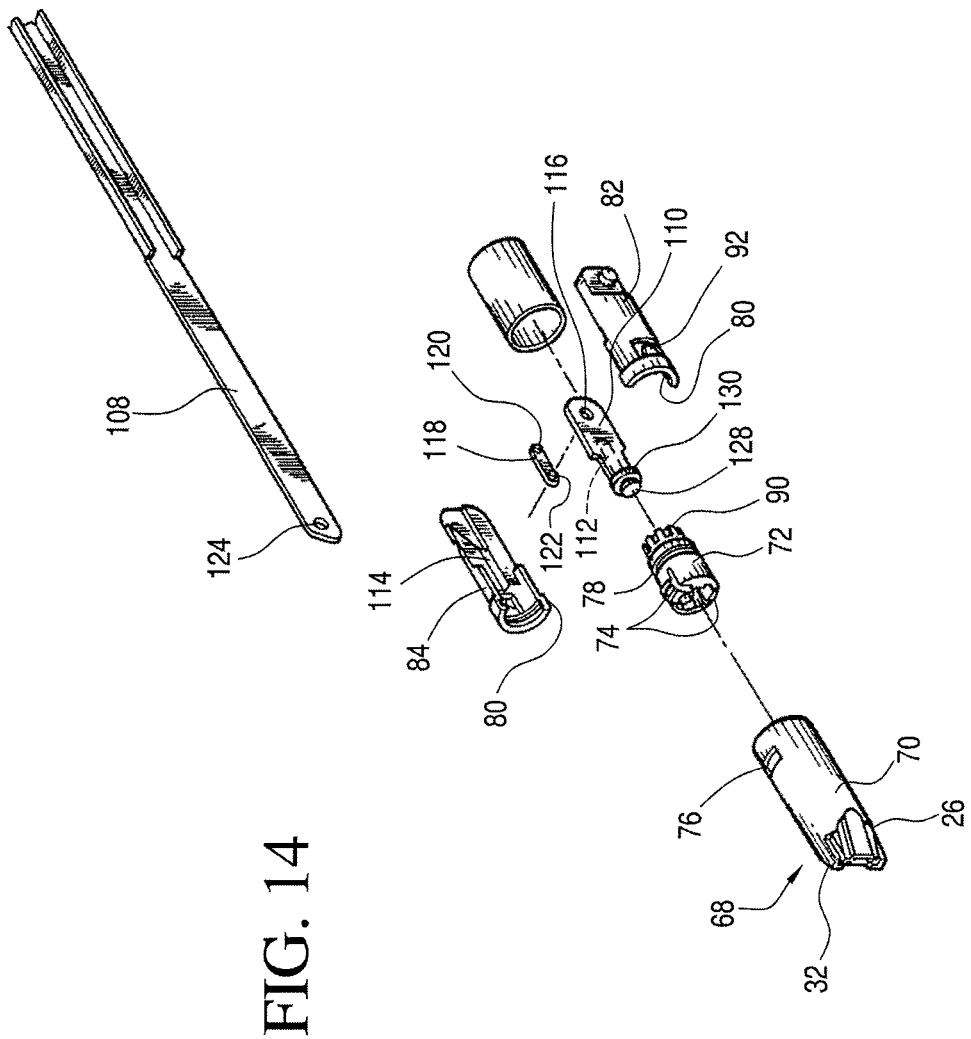
FIG. 14 is an exploded view showing various elements associated with the staple forming mechanism of the present surgical stapler.
Figure 15:
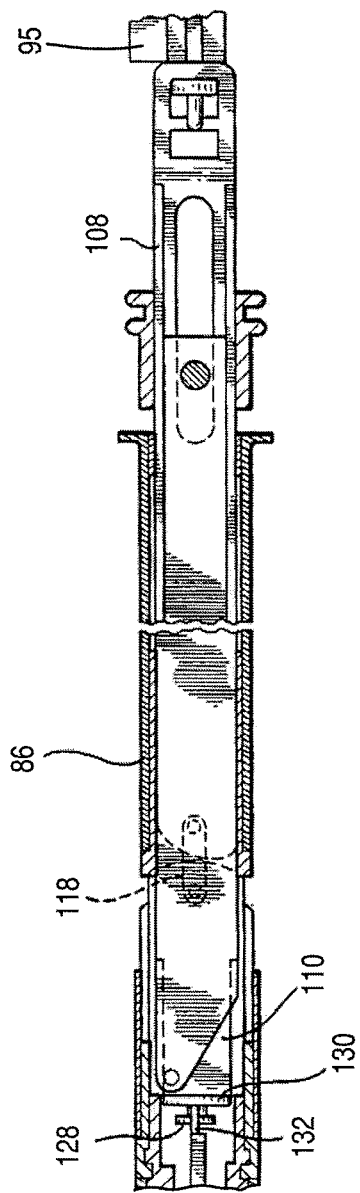
FIG. 15 is a cross sectional view showing the driving components of the surgical stapling device.
Figure 16:
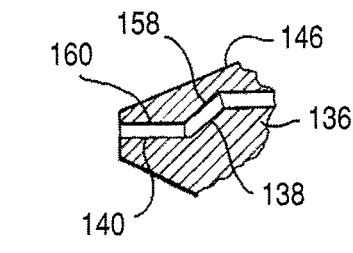
FIGS. 16, 17, 18, 19, 20 and 21 are various views of the present staple cartridge employed in accordance with the present surgical stapling device.
Figure 17:
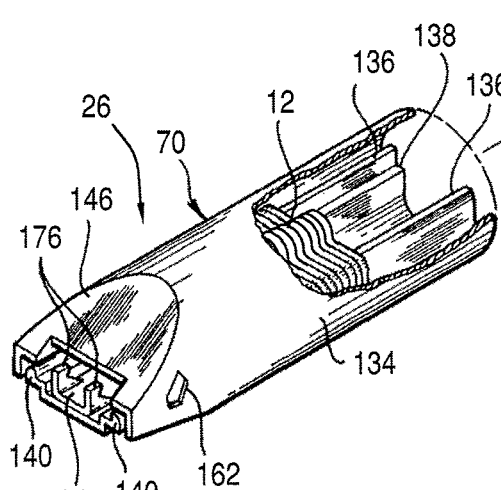
Figure 18:
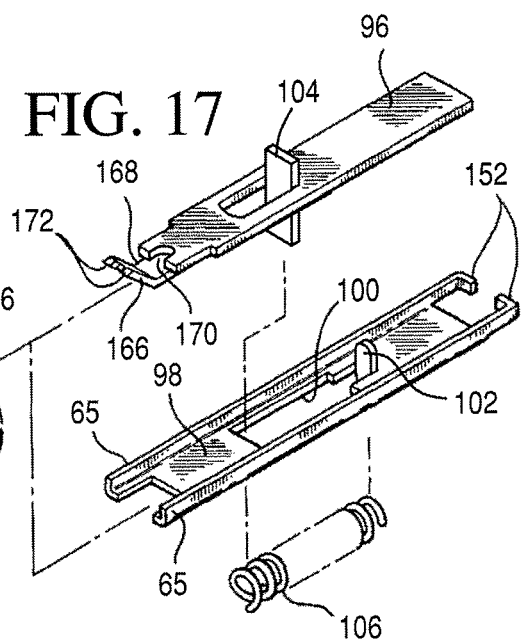
Figure 19:
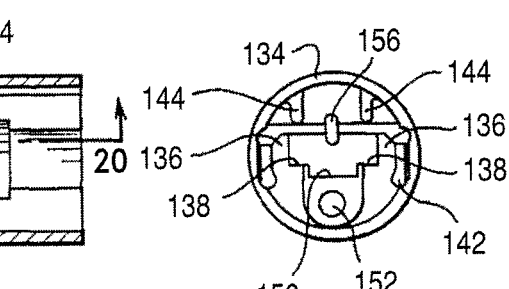
Figure 20:
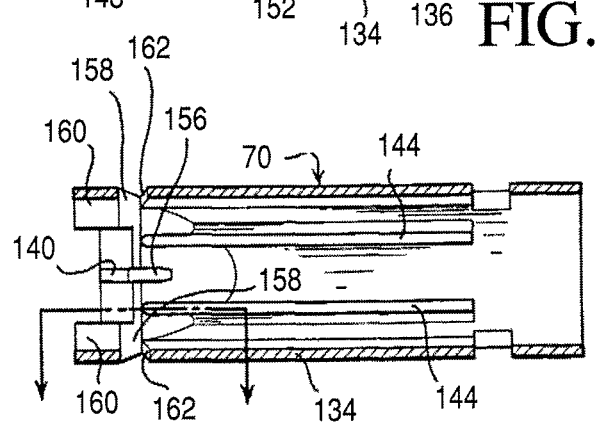
Figure 21:
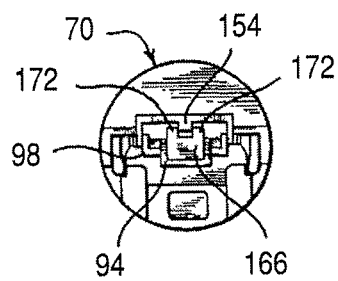

If, however, it is desired to lock the staple 12 relative to suture 14 by crimping the crimp loop 22 about the suture 14, and with reference to FIGS. 11, 12, and 13, a crimping arm 200 is moved forward by movement of actuation arm 201 and into engagement with the crimp loop 22 such that the distal end of the crimping arm 200 engages the crimp loop 22 in a manner which deforms the crimp loop 22 into engagement with the suture 14. With this in mind, the crimping arm 200 includes a recess 202 at its distal end which is shaped and dimensioned to fit about the crimp loop 22 and cause deformation thereof as the crimping arm 200 is moved forward under the control of the operator. More particularly, the crimping arm 200 is composed of an outer crimping arm member 200a and an inner crimping arm member 200b. The outer crimping arm member 200a moves relative to the inner crimping arm member 200b to compress the distal end of the inner crimping arm member 200b about the crimp loop 22 for closing it about the suture 14. Once crimping is completed the staple actuating lever and actuation arm 201 are released by sliding release lever 203.

After the staple holder 96 and the staple former 98 are fully advanced to form one of the staples 12, the staple actuating lever 212 is released and returned to its original position by the return coil spring, which retracts the slide block (not shown) and the staple driver 108.

Once the staple actuating lever 212 is released (whether prior to crimping or after crimping) the staple former 98 is moved rearwardly relative to the staple holder 96 by the compression coil spring 106. When the depending prong 104 of the staple holder 96 is engaged by the front edge of the slot 100 of the staple former 98, the staple holder 96 and the staple former 98 are retracted together by the return spring (not shown) in the actuator handle assembly. The ejector arm 166 lifts the formed staple 12 from the anvil prongs 176 as the staple holder 96 is retracted. The staple holder 96 and the staple former 98 are returned to the start position shown where the next staple 12 is received in the notch 168 in front of the pusher finger 170. Then the staple forming cycle is repeated to form the next staple 12.

Further to the description of the staple forming procedure as described above, the three configurations of the staple 12 are shown with reference to FIGS. 22, 23 and 24. In its initial shape, the staple 12 includes a central support body (or backspan) 16 from which two depending legs 18, 20 extend at the distal ends thereof. At the center portion of the backspan 16 is a crimp loop 22 which is ultimately crimped for securing the suture in the manner described herein.

It is intended the present surgical stapling device 10 can be the distal end effector of a surgical instrument for use in open, laparoscopic, and/or endoscopic surgical procedures. The present design is shown with a maximum diameter of 13 mm and a rigid length of 31.75 mm, which is easily accommodated for use in a transesophageal access approach. Articulation in an endoscopic device is accomplished by mating a device with a steerable overtube, or by providing a proximal effector with its own steering. In accordance with a preferred embodiment as disclosed herein, the fastener applier has space to accommodate vacuum, lighting and visualization capabilities. Laparoscopic devices will ideally have the ability to articulate built into the proximal end effector.

For example, another use for the present surgical stapler is for the closure of perforations, ulcerations and intentional incisions or otomies (gastrotomy, colostomy, etc.). To close such a defect, a crimped staple with a first end of a suture crimped thereto (that is, fixedly coupled thereto) is placed at one end of the opening. Uncrimped staples are then applied on alternating sides of the opening along its entire length. The last staple is then placed. Prior to crimping the suture into engagement with the last applied staple, the suture is tensioned in the system approximating the tissue closing the defect. Once tensioned, the staple is crimped onto the suture locking it into place. The process can be repeated inverting or everting the defect as surrounding tissues are brought into contact around the initial defect.

Figure 25:
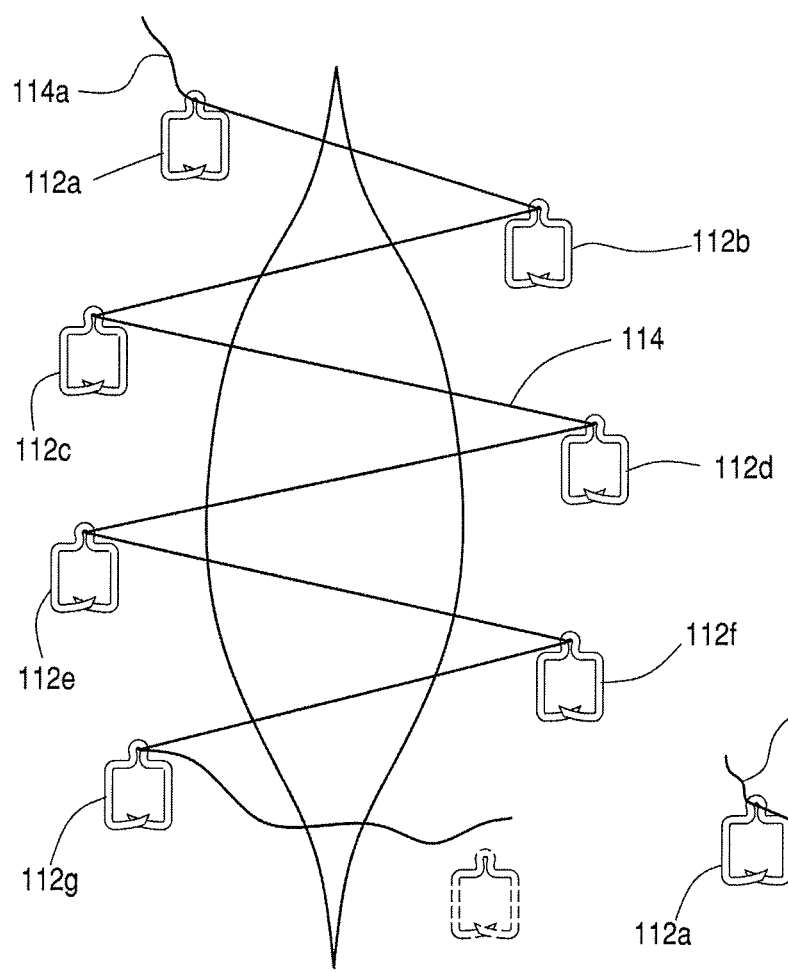
FIGS. 25 and 26 show the application of a series of staples used in forming a tissue fold in accordance with the present invention.
Figure 26:
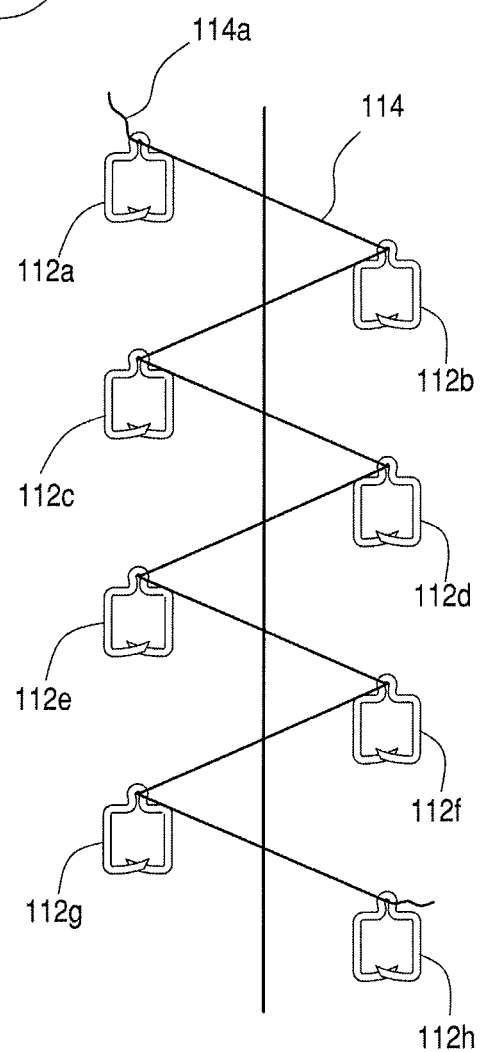

Referring to FIGS. 25 and 26, a similar technique may be utilized in the formation of plications along the stomach wall as part of a gastric volume reduction procedure. In particular, to form such a fold, a crimped staple 112a with a first end 114a of a suture 114 crimped thereto (that is, fixedly coupled thereto) is placed at one end of the opening stomach wall where a plication (that is, a fold) is desired. Uncrimped staples 112b-g are then applied on alternating sides of the desired fold location along the entire length of the fold location. The length of suture 114 is therefore, snared within the staples 112b-h but is free to move relative to the staples 112b-g for cinching the length of suture 114 as will be described below in greater detail. The last staple 112h is then placed. Prior to crimping the suture 114 into engagement with the last applied staple 112h, the suture 114 is tensioned in the system approximating the tissue and forming a plication along the stomach wall. Once tensioned, the final staple 112h is crimped onto the suture 114 locking it into place and holding the plication in its desired configuration. This procedure is described in greater detail in commonly owned and co-pending U.S. patent application Ser. No. 11/779,314, filed Jul. 18, 2007, entitled "HYBRID ENDOSCOPIC/LAPAROSCOPIC DEVICE FOR FORMING SEROSA TO SEROSA PLICATIONS IN A GASTRIC CAVITY", and Ser. No. 11/779,322, FILED Jul. 18, 2007, entitled "HYBRID ENDOSCOPIC/LAPAROSCOPIC METHOD FOR FORMING SEROSA TO SEROSA PLICATIONS IN A GASTRIC CAVITY", which are hereby incorporated herein by reference.

It is further contemplated that the present fastener applier may be utilized in attaching a suture to tissue to apply traction to it, creating a suspension between two points on which a tissue rests or is retracted, and/or staging, positioning or tacking tissues into a configuration to be reinforced by another device (stapler, adhesive, or other fastener).

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used system is obtained and if necessary cleaned. The system can then be sterilized. In one sterilization technique, the system is placed in a closed and sealed container, such as a plastic or TYVEK bag. The container and system are then placed in a field of radiation that can penetrate the container, such as gamma radiation, x-rays, or high-energy electrons. The radiation kills bacteria on the system and in the container. The sterilized system can then be stored in the sterile container. The sealed container keeps the system sterile until it is opened in the medical facility.

It is preferred that the device is sterilized. This can be done by any number of ways known to those skilled in the art including beta or gamma radiation, ethylene oxide, and/or steam.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A surgical stapling device, comprising:
an actuator handle assembly coupled to a staple head assembly;
the staple head assembly including a dispensing, first end and a cartridge housing adapted to receive a plurality of staples in a row for longitudinal movement therethtough, an anvil mounted on the cartridge housing; a mechanism for advancing the forwardmost staple in the row toward the dispensing, first end of the staple head assembly and into engagement with the anvil; and a suture guide including a guide track supporting art exposed length of suture that extends in a loop from a proximal end of the surgical stapling device for selective attachment to the staples as the staples are deployed, wherein the staple head assembly further includes a crimping arm suture and each staple includes a crimp loop in which the length of suture is positioned, the crimping arm selectively engaging the crimp loop to securely lock the staple relative to the length of suture by compressing the crimp loop such that the crimp loop may take a slidable configuration or a locked configuration.

2. The surgical stapling device according to claim 1, including a staple former for forming the forwardmost staple about the anvil.

3. The surgical stapler according to claim 1, wherein each of the staples includes a backspan with first and second legs, and the backspan of the staple is provided with a crime loop shaped and dimensioned for receiving and securing the suture.

4. A surgical stapling device, comprising:
an actuator handle assembly coupled to a staple head assembly;
the staple head assembly including a cartridge housing adapted to receive a plurality of staples in a row for longitudinal movement therethrough, an anvil mounted on the cartridge housing;
a mechanism for advancing the forwardmost staple in the row into engagement with the anvil; and
a suture guide supporting a length of suture that extends in a loop for selective attachment to the staples as the staples are deployed;
wherein each staple includes a crimp loop and the surgical stapling device further includes a crimping arm which selectively engages the crimp loop to securely lock the staple relative to the length of suture.

5. The surgical stapling device according to claim 4 wherein the crimping arm includes an outer crimping arm member and an inner crimping atm member.

6. The surgical stapling device according to claim 5, wherein the outer crimping arm member moves relative to the inner crimping arm member to compress a distal end of the inner crimping arm member about the crimp loop for closing the crimp mop about the suture.

7. A surgical stapling device, comprising:
an actuator handle assembly coupled to a staple head assembly;
the staple head assembly including a cartridge housing adapted to receive a plurality of staples in a row for longitudinal movement therethrough, an anvil mounted on the cartridge housing;
a mechanism for advancing the forwardmost staple in the row into engagement with the anvil;
a suture guide supporting a length of suture that extends in a loop for selective attachment to the staples as the staples are deployed; and
further including a crimping arm which selectively engages the suture to securely lock the staple relative to the suture.

8. The surgical stapling device according to claim 7, wherein the crimping arm includes an outer crimping arm member and an inner crimping arm member.

9. The surgical stapling device according to claim 8, wherein the outer crimping arm member moves relative to the inner crimping arm member to compress a distal end of the inner crimping arm member about the staple for closing the staple about the suture.

* * * * *